(12) United States Patent
Battarbee et al.

(10) Patent No.: US 6,291,824 B1
(45) Date of Patent: Sep. 18, 2001

(54) APPARATUS AND METHOD FOR HIGH-BANDWIDTH OPTICAL TOMOGRAPHY

(75) Inventors: Harold D. Battarbee; Juan G. Rodriguez, both of Shreveport, LA (US)

(73) Assignees: Board of Supervisors of Louisiana State University and Agricultural and Mechanical College, Baton Rouge; Centenary College of Louisiana, Shreveport, both of LA (US)

( * ) Notice: Subject to any disclaimer, the term of this patent is extended or adjusted under 35 U.S.C. 154(b) by 0 days.

(21) Appl. No.: 09/288,753

(22) Filed: Apr. 8, 1999

Related U.S. Application Data

(60) Provisional application No. 60/135,111, filed on Apr. 13, 1998.

(51) Int. Cl.$^7$ .................................................... G01N 21/00
(52) U.S. Cl. ........................................ 250/330; 250/341.7
(58) Field of Search .................................... 250/330, 332, 250/339.02, 339.06, 339.12, 341.1, 341.7; 356/435; 600/504, 310

(56) References Cited

U.S. PATENT DOCUMENTS

| | | | |
|---|---|---|---|
| 4,386,854 | * | 6/1983 | Byer ..................................... 356/438 |
| 5,798,840 | * | 8/1998 | Beiting ................................ 356/437 |
| 6,111,645 | * | 8/2000 | Tearney et al. ..................... 356/354 |

OTHER PUBLICATIONS

Kurth et al., "A Dynamic Phantom Brain Model for Near–Infrared Spectroscopy," *Phys. Med. Biol.*, vol. 40, pp. 2079–2092 (1995).

Li, X. et al., "Diffration Tomography for Biochemical Imaging with Diffuse–Photon Density Waves," *Opt. Lett.*, vol. 22, pp. 573–575 (plus errata) (1997).

McCormick, P., "Intracerebral Penetration of Infrared Light," *J. Neurosurg.*, vol. 76, pp. 315–318 (1992).

Model, R. et al., "Reconstruction Algorithm for Near–Infrared Imaging in Turbid Media by Means of Time–Domain Data," *J. Opt. Soc. Am. A*, vol. 14, pp. 313–324 (1997).

Müller, G. et al., "Laser–Generated Diffusion Tomograms in the Near Infrared," *Laser Physics*, vol. 6, pp. 589–595 (1996).

(List continued on next page.)

*Primary Examiner*—Georgia Epps
*Assistant Examiner*—Richard Hanig
(74) *Attorney, Agent, or Firm*—John H. Runnels

(57) ABSTRACT

An apparatus and method for dramatically increasing the imaging rate of optical tomography are disclosed. The novel technique is based on precise, time-resolved measurements. Measurements may optionally be taken at different wavelengths more-or-less simultaneously with a single device. A stationary array of emitters and a stationary array of detectors are located around the sample. High bandwidth is achieved by rapidly delivering light signals (single pulses or bursts of periodic pulses) in sequence from discrete, stationary emitters positioned around the sample, and rapidly detecting signals transmitted through the sample by discrete, stationary detectors. Bandwidths on the order of megahertz are possible in imaging biolgical sample. By selecting appropriate illuminating wavelengths, the system may be used, for example, to rapidly image the state of, and changes in, such characteristics as blood volume, blood flow, oxygen saturation, cellular depolarization, cellular repolarization, and tissue redox state. In addition to eliminating any requirement for mechanical scanning, the novel system allows the position of the fiber arrays to be chosen to fit the contour of the sample.

15 Claims, 6 Drawing Sheets

OTHER PUBLICATIONS

O'Leary, M. et al., "Experimental Images of Heterogeneous Turbid Media by Frequency–Domain Diffusing–Photon Tomography," *Optics Lett.*, vol. 20, pp. 426–428 (1995).

Okada, F. et al., "Impaired Interhemispheric Integration in Brain Oxygenation and Hemodynamics in Schizophrenia," *Eur. Arch. Psych. Clin. Neurosci.*, vol. 224, pp. 17–25 (1994).

Rossetto, M. et al., "A Simple Nanosecond Gate for Side Window Photomultipliers and Echoes in Such Photomultipliers," *Rev. Sci. Instr.*, vol. 43, pp. 1244–1246, (1972).

Sevick, E. et al., "Quantitation of Time– and Frequency–Resolved Optical Spectra for the Determination of Tissue Oxygenation," *Anal. Biochem.*, vol. 195(2), pp. 330–351 (1991).

Takada, M. et al. (Shimadzu Corporation), "Optical Tomographic Image System," *technical paper* (Jun. 22, 1995, English translation).

Villringer, A. et al., "Non–invasive optical spectroscopy and imaging of human brain function," *Trends Neurosci.*, vol. 20, pp. 435–442 (1997).

Walker, S., "Image Reconstruction by Backprojection from Frequency–Domain Optical Measurements in Highly Scattering Media," *Appl. Opt.*, vol. 36, pp. 170–179 (1997).

Yodh, A. et al., "Spectroscopy and Imaging with Diffusing Light," *Physics Today*, pp. 34–40 (Mar. 1995).

Zhu, X. et al., "Imaging Objects in Tissuelike Media with Optical Tagging and the Diffuse Photon Differential Transmittance," *J. Opt. Soc. Am. A.*, vol. 14, pp. 300–305 (1997).

Benaron et al., "Optical Time–of–Flight and Absorbance Imaging of Biologic Media," *Science*, vol. 259, pp. 1463–1466 (1993).

Chance, B. et al., "Cognition–Activated Low–Frequency Modulation of Light Absorption in Human Brain," *Proc. Natl. Acad. Sci. USA*, vol. 90, pp. 3770–3774 (1993).

Colak, S., "Tomographic Image Reconstruction from Optical Projections in Light–Diffusing Media," *Appl. Opt.*, vol. 36, pp. 180–213 (1997).

Cubeddu, R. et al., "Imaging of Optical Inhomogeneities in Highly Diffusive Media: Discrimination between Scattering and Absorption Contributions," *Appl. Phys. Lett.*, vol. 69, pp. 4162–4164 (1996).

Elwell, C. et al., "Quantification of Adult Cerebral Hemodynamics by Near–infrared Spectroscopy," *J. Appl. Physiol.*, vol. 77, pp. 2753–2760 (1994).

Gandjbakhche, A. et al., "Resolution Limits for Optical Transillumination of Abnormalities Deeply Embedded in Tissues," *Med. Phys.*, vol. 21, pp. 185–191 (1994).

Grable, R., "Optical Tomography Improves Mammography," *Laser Focus World*, pp. 113–118 (Oct. 1996)

Grosenick, D. et al., "Time–Resolved Imaging of Solid Phantoms for Optical Mammography," *Appl. Opt.*, vol. 36, pp. 221–231 (1997).

Hebden, J. et al., "Imaging through Scattering Media by the Use of an Analytical Model of Perturbation Amplitudes in the Time Domain," *Appl. Opt.*, vol. 35, pp. 6788–6796 (1996).

Hebden, J., "The Spatial Resolution Performance of a Time–Resolved Optical Imaging System using Temporal Extrapolation," *Med. Phys.*, vol. 22, pp. 201–208 (1995).

Hebden, J. et al., "Time–Resolved Optical Tomography," *Appl. Opt.*, vol. 32, pp. 372–380 (1993).

Jobin, A., "Method of Calculating the Image Resolution of a Near–Infrared Time–of–Flight Tissue–Imaging System," *Appl. Opt.*, vol. 35, pp. 752–757 (1996).

Jöbsis, F. "Myocardial Oxygen Sufficiency and Circulatory Parameters," *Science*, vol. 198, pp. 1264–1267 (1977).

Kooijman, H. et al., "Near Infrared Spectroscopy for Noninvasive Assessment of Claudication," *J. Surg. Res.*, vol. 72, pp. 1–7 (1997).

\* cited by examiner

APPARATUS AND METHOD FOR HIGH-BANDWIDTH OPTICAL TOMOGRAPHY

The benefit of the Apr. 13, 1998 filing date of provisional application No. 60/135,111 is claimed under 35 U.S.C. § 119(e).

This invention pertains to the rapid imaging of samples such as living biological tissues, particularly to imaging by optical tomography.

Biological tissues, particularly mammalian tissues, are relatively permeable to light in the near infrared (NIR) spectrum (~700–900 nm). Photon transport through tissue at these wavelengths is dominated by scattering rather than by absorption. What light absorption does occur in this region is primarily attributable to the heme groups of hemoglobin. Deoxyhemoglobin and oxyhemoglobin have different NIR absorption spectra. These differences have been exploited in commercial "oximeters," devices that non-invasively monitor hemoglobin oxygen saturation. Existing oximeters measure global changes in hemoglobin saturation and blood volume, but do not resolve spatial details.

Conventional geometrical optics cannot be employed with infrared oximetry to image discrete hypoxic regions, especially deeper regions, because of the turbid nature of mammalian tissue. Prior suggestions to overcome these limitations have included proposals for time-resolved and frequency methods. In the time-resolved method, the path and time of flight of a photon through tissue depend on the absorptive and scattering substances inside the turbid sample. The different trajectories of photons through the tissue require different lengths of time to reach a detector because of their different path lengths. Direct-flight or "ballistic" photons arrive at the detector first, followed by scattered photons that have taken longer paths. Absorbed photons, of course, are not detected at all. Examining the temporal distribution of detected photons reveals information about what lies in the path between the emitter and the detector. For example, an absorbing occlusion in the direct path between the emitter and the detector would absorb "ballistic" photons preferentially, while photons that scattered around the occlusion could still reach the detector, although at a later time. Similarly, the frequency-domain method, which uses an intensity-modulated light emitter with a detection system tuned to the modulation frequency, relies on phase and amplitude changes between the emitter and the detector to locate inhomogeneities inside the sample. In both the time-resolved and the frequency,-domain methods, images of the interior of the sample may be constructed by moving the axis between the emitter and the detector across the sample. All known prior NIR tomographic imaging techniques have used mechanical scanning to reposition the emitter, the detector, or the sample. The mechanical scanning limits the speed at which data may be acquired.

R. Grable, "Optical Tomography Improves Mammography," *Laser Focus World*, pp. 113–118 (October 1996) discloses an optical tomography system for mammography, in which laser light was delivered by an optical fiber to a rotating polygon mirror, producing a fan beam, and the detector consisted of an array of several hundred avalanche photoditodes. In an alternative embodiment, the avalanche photodiodes were replaced with large-area photodiodes, laser illumination was provided by a single beam, and the detectors and laser beam orbited around the object being scanned. The author noted that construction of suitable scanning apparatus was not trivial; that the rotary motion of the lager beam and detectors must be precise.

X. Zhu et al., "Imaging Objects in Tissuelike Media with Optical Tagging and the Diffuse Photon Differential Transmittance," *J: Opt. Soc. Am. A*, vol. 14, pp. 300–305 (1997) discloses measuring differential transmittance of light through a scattering medium at two different wavelengths to enhance the ability to image optically-tagged objects within the scattering medium.

J. Hebden et al., "Time-Resolved Optical Tomography," *Appl. Opt.*, vol. 32, pp. 372–380 (1993) discloses the use of time-resolved optical tomography to image objects inside a scattering medium by measuring only transmitted photons having the shortest time of flight, i.e., the small fraction of photons that travels through the sample in approximately a straight line.

P. McCormick, "Intracerebral Penetration of Infrared Light," *J. Neurosurg.*, vol. 76, pp. 315–318 (1992) presents one of the earlier reports on the transmission of near-infrared light through human cerebral tissue, and on the application of such techniques to the measurement of hemoglobin and hemoglobin oxygen saturation. See also F. Okada et al., "Impaired Interhemispheric Integration in Brain Oxygenation and Hemodynamics in Schizophrenia," *Eur. Arch. Psych. Clin. Neurosci.*, vol. 244, pp. 17–25 (1994).

M. Takada et al. (Shimadzu Corporation), "Optical Tomographic Image System," technical paper (Jun. 22, 1995, English translation) describes in general terms an optical tomographic imaging system, its components, and experiments performed with the system.

S. Colak, "Tomographic Image Reconstruction from Optical Projections in Light-Diffusing Media," *Appl. Opt.*, vol. 36, pp. 180–213 (1997); and S. Walker, "Image Reconstruction by Backprojection from Frequency-Domain Optical Measurements in Highly Scattering Media," *Appl. Opt.*, vol.36, pp. 170–179 (1997); disclose algorithms for reconstructing the location and optical properties of objects in a scattering medium following measurements with near infrared light.

A. Gandjbakhche et al., "Resolution Limits for Optical Transillumination of Abnormalities Deeply Embedded in Tissues," *Med. Phys.*, vol. 21, pp. 185–191 (1994); J. Hebden, "The Spatial Resolution Performance of a Time-Resolved Optical Imaging System using Temporal Extrapolation," *Med. Phys.*, vol. 22, pp. 201–208 (1995); and A. Jobin, "Method of Calculating the Image Resolution of a Near-Infrared Time-of-Flight Tissue-Imaging System," *Appl. Opt.*, vol. 35, pp. 752–757 (1996) discuss spatial resolution in reconstructing the location and optical properties of objects in a scattering medium following measurements with near infrared light, including measurements made with both "line-of-sight" photons and with photons scattered along a somewhat longer path than line-of-sight.

E. Sevick et al., "Quantitation of Time- and Frequency-Resolved Optical Spectra for the Determination of Tissue Oxygenation," *Anal. Biochem.*, vol. 195(2), pp. 330–351 (1991) discusses algorithms for the quantitation of hemoglobin saturation from photon decay rates obtained from dual wavelength, time-resolved and frequency-resolved spectra using multiple emitters and detectors. This reference discusses only means for measuring absorptivity, not for acquiring images. The authors noted that the instrument was slow (requiring more than 30 seconds for one measurement).

D. Benaron et al., "Optical Time-of-Flight and Absorbance Imaging of Biologic Media," *Science*, vol. 259, pp. 1463–1466 (1993) discloses an optical tomography technique using a variable-interval time collection window for photons arriving at the detector, to collect photons until a fixed percentage of the total transmitted photons had been received. Images were made both of model systems, and of internal structure of a dead, 10-day-old rat pup suspended in blood.

G. Müller et al., "Laser-Generated Diffusion Tomograms in the Near Infrared," *Laser Physics*, vol. 6, pp. 589–595 (1996) discloses a method for laser-generated tomography using photon density waves and an algorithm for reconstructing the image. An optical tomogram of a rat brain ex vivo without skull was illustrated. See also M. O'Leary et al., "Experimental Images of Heterogeneous Turbid Media by Frequency-Domain Diffusing-Photon Tomography," *Optics Lett.*, vol. 20, pp. 426–428 (1995).

A. Yodh et al., "Spectroscopy and Imaging with Diffusing Light," *Physics Today*, pp. 34–40 (March 1995) provides an overview of techniques currently available using near infrared light for imaging and spectroscopy of biological specimens.

There has been recent interest in developing optical devices that can monitor tissue function, and that can display the measurements as cross-sectional images. If an effective means were available by which the optical properties of tissue could be measured rapidly in a tomographic manner, it would be possible to image many functional parameters, such as tissue perfusion, sudden blood volume changes, and cell depolarization and repolarization. This imaging capability would also permit real-time images of hypoxic regions and hematomas. Imaging tissue perfusion, for example, requires a scanner sufficiently fast to follow changes that ensue from the infusion of a tracer into the bloodstream, changes that can occur on a time scale of tenths of seconds. See, e.g., C. Elwell et al., "Quantification of Adult Cerebral Hemodynamics by Near-infrared Spectroscopy," *J: Appl. Physiol.*, vol. 77, pp. 2753–2760 (1994); and H. Kooijman et al., "Near Infrared Spectroscopy for Noninvasive Assessment of Claudication," *J. Surg. Res.*, vol. 72, pp. 1–7 (1997). Imaging brain cortex activity, by monitoring blood volume changes or cell depolarization/repolarization, requires scanning bandwidths of several Hz for the former or kHz for the latter. See, e.g., B. Chance et al., "Cognition-Activated Low-Frequency Modulation of Light Absorption in Human Brain," *Proc. Natl. Acad. Sci. USA*, vol. 90, pp. 3770–3774 (1993); and A. Villringer et al., "Non-invasive optical spectroscopy and imaging of human brain function," *Trends Neurosci.*, vol. 20, pp. 435–442 (1997). However, no effective means to achieve such high bandwidths with an optical scanner has previously been available. There is an unfilled need for optical tomographic techniques capable of high image acquisition rates.

We have discovered an apparatus and method for dramatically increasing the imaging rate of optical tomography. The novel technique is based on time-resolved measurements. Measurements may optionally be taken at different wavelengths more-or-less simultaneously with a single device. A stationary array of emitters and a stationary array of detectors are located around the sample. High bandwidth is achieved by rapidly delivering light signals (single pulses or bursts of periodic pulses) in sequence from discrete, stationary emitters positioned around the sample, and rapidly detecting signals transmitted through the sample by discrete, stationary detectors. Bandwidths on the order of megahertz are possible in imaging biological samples. By selecting appropriate illuminating wavelengths, the system may be used, for example, to rapidly image the state of, and changes in, such characteristics as blood volume, blood flow, oxygen saturation, cellular depolarization, cellular repolarization, and tissue redox state. In addition to eliminating any requirement for mechanical scanning, the novel system allows the position of the fiber arrays to be chosen to fit the contour of the sample.

BRIEF DESCRIPTION OF THE DRAWINGS

FIG. 6(*b*) displays the results of processing data for ballistic photons through a simple tomographic algorithm to indicate the presence and location of the occlusion in the sample shown in FIG. 6(*a*).

FIG. 6(*c*) displays the same type of result as shown in FIG. 6(*b*), except that data from non-ballistic photons were used instead.

Figure 1A:
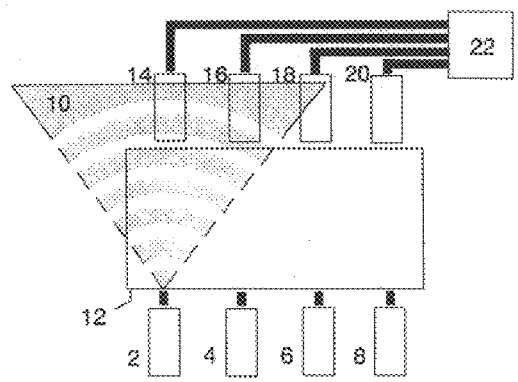
FIGS. 1(*a*)–(*d*) illustrate schematically the novel approach to high-bandwidth optical tomography.
Figure 1B:
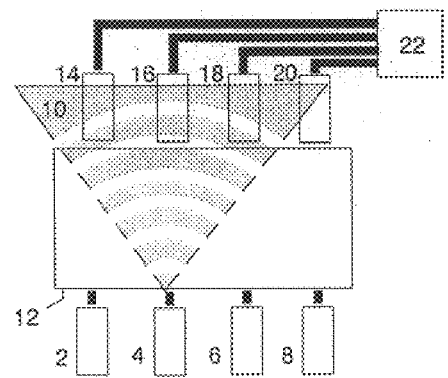
Figure 1C:
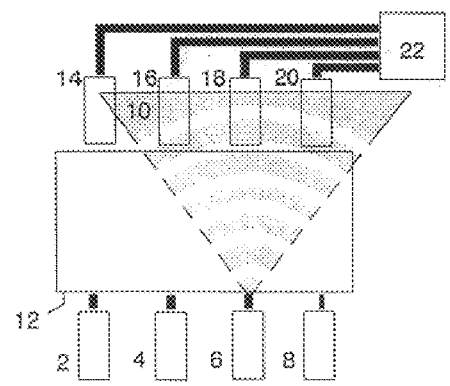
Figure 1D:
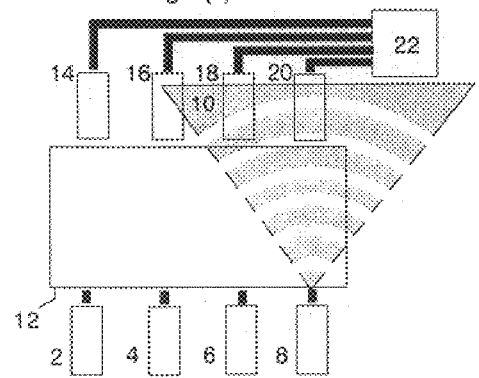

Each emitter in the stationary array produces a light pulse or a burst of pulses directed at the target. The different emitters are activated in rapid sequence. An array of stationary detectors captures light after it passes through the target or sample. Each of the detectors can detect light originating from each of the emitters. The output of each detector is connected to the input channel of a high-bandwidth, multichannel digitizer that records all detected signals in real-time.

FIGS. 1(*a*)–(*d*) illustrate schematically the novel approach to high-bandwidth optical tomography. As shown in FIG. 1(*a*), a first pulse of interrogating radiation 10 starts at stationary emitter 2, passes through sample 12, and is detected by stationary detectors 14, 16, 18, and 20. After amplification, the detected signals are transmitted to processing electronics and computer 22. As shown in FIGS. 1(*b*)–(*d*), after short delays the process is repeated from emitters 4, 6, and 8. Because of the delays between pulses from the different emitters, the timing of the pulses arriving at detectors 14, 16, 18, and 20 indicates the position of the emitter from which each pulse began. After processing with an appropriate tomographic algorithm, the recorded information yields spatial resolution of absorption and scattering parameters.

The emitters are activated in rapid sequence, preferably at time intervals sufficiently short to insure that the train of signals falls within one trace of the recording digitizer. The time interval between successive emitter activations should be sufficiently large that light from only a single emitter pulse can traverse the sample at any given time to avoid emitter-detector cross-talk, as illustrated in FIGS. 1(*a*)–(*d*). For most applications in time-resolved tomography, an interval of about 5 ns between pulses from successive emitters suffices to insure that there is no significant temporal overlap of light pulses within the sample.

A frequency-domain method may be used with the novel tomographic technique in at least two ways. One way is to Fourier-transform the time-resolved signals recorded by the digitizer. The resulting frequency-domain information will be distributed over many modulation frequencies due to the short duration of the signals used in the time-domain measurements. The other way is to replace the pulses of light with short bursts of modulated light. The second alternative increases the strength of the signal within a narrower range of frequencies. Again, the minimum time interval between bursts of modulated light in many applications is about 5 ns.

Figure 2:
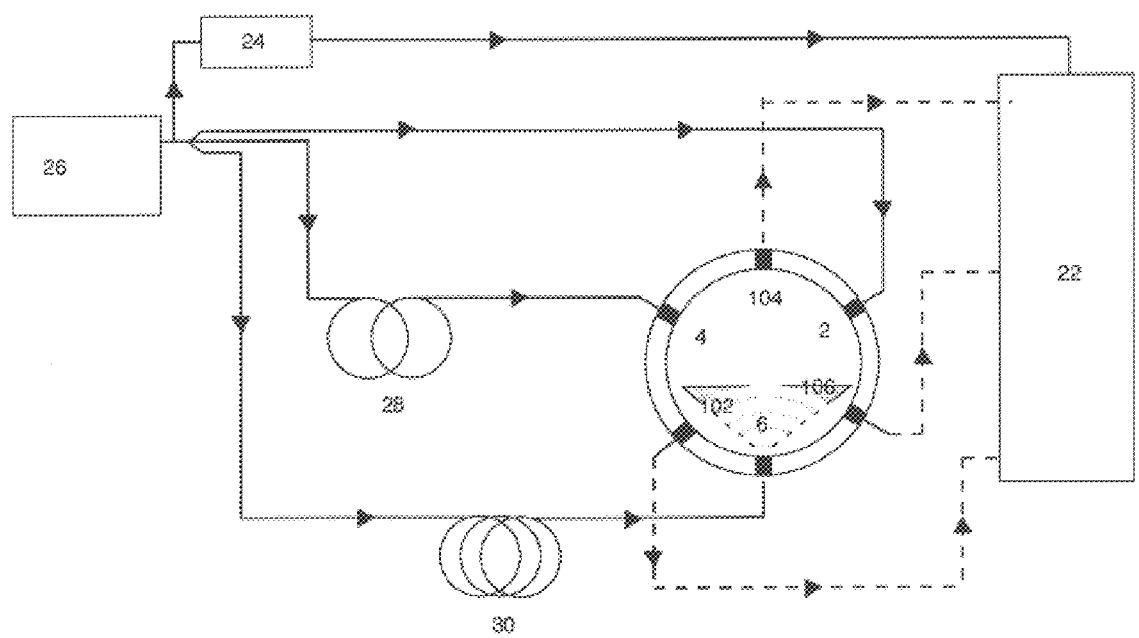
FIG. 2 illustrates one embodiment of a time-resolved tomograph in accordance with this invention, in which one laser pulse is used per tomographic image.

As illustrated in FIG. 2, one embodiment of a lime-resolved tomograph in accordance with this invention employs two arrays of optical fibers, one array (fibers 2, 4, and 6) to deliver light signals to the target, and one array (fibers 102, 104, and 106) to collect light signals from the target. The first array serves as the emitters by guiding photons from a common pulsed laser light source 26 to loci 2, 4, and 6 around the sample. The second array 102, 104, and 106 serve as detectors by guiding collected light from loci around the target to photomultiplier tubes and processing electronics 22. Processing electronics 22 also receives an optical triggering input 24 responsive to laser 26. Time delays between the delivery of emitted pulses arc readily generated optically by adjusting the lengths of the deliver fibers, as shown schematically by loops 28 and 30.

Figure 3:
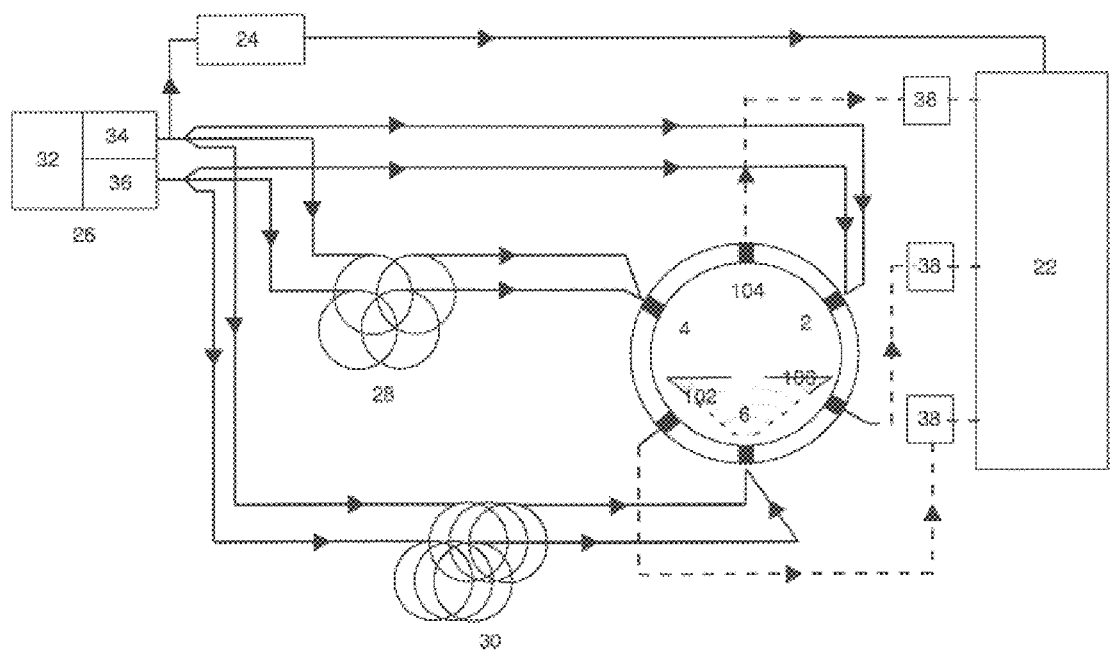
FIG. 3 illustrates another embodiment of a time-resolved tomograph in accordance with this invention, a dual-wavelength, high-bandwidth optical tomograph, in which one laser pulse at each of two frequencies is used per tomographic image.

A second embodiment is shown in FIG. 3, depicting a dual-wavelength, high-bandwidth optical tomograph for probing nine axes in a plane. Numbering of parts is as in FIG. 2, except as otherwise mentioned. The, output of laser 32 is split to pump two near-infrared dye lasers 34 and 36 simultaneously, generating synchronized pulse outputs at two different wavelengths $\lambda_1$ and $\lambda_2$. Each of the two dye-laser outputs is focused into a trifurcated fiber optic bundle. The output laser pulses are carried by fiber optics to emitter sites 2, 4, and 6. Each of the fibers has a different length, so that each pair of the six pulses arrives at a slightly different time. Each detector 102, 104, or 106 therefore senses a train of three pairs of pulses for each initial pulse from the pump laser. Because light propagates through most biological targets of interest in 5 nanoseconds or less, this time may be adopted as the minimum temporal spacing between emitter pulses. The device shown in FIG. 3 can thus produce absorption and scattering information along nine axes, 2-102 at $\lambda_1$, 2-104 at $\lambda_1$, 2-106 at $\lambda_1$, 4-102 at $\lambda_1$, 4-104 at $\lambda_1$, 4-106 at $\lambda_1$, 6-102 at $\lambda_1$, 6-104 at $\lambda_1$, 6-106 at $\lambda_1$, 2-102 at $\lambda_2$, 2-104 at $\lambda_2$, 2-106 at $\lambda_2$, 4-102 at $\lambda_2$, 4-104 at$\lambda_2$, 4-106 at $\lambda_2$, 6-102 at $\lambda_2$, 6-104 at $\lambda_2$, and 6-106 at $\lambda_2$, all in a total time as short as about 90 nanoseconds.

Preferably, the time between subsequent pulses from different emitters (during a single cycle) is between about 5 nanoseconds and about 100 milliseconds. Preferably, the time between subsequent cycles is between about 1 microsecond and about 1 second.

The number of emitters and detectors may readily be increased, three of each being shown here for illustrative purposes. As the number of emitter-detector combinations increases, so does the resolution of the images generated. Eventually, the system should reach an optimum resolution of about 0.5 cm, based on theoretical calculations for NIR tomography. See J. Hebden, "The Spatial Resolution Performance of a Time-Resolved Optical Imaging System using Temporal Extrapolation," Med. Phys., vol. 22, pp. 201–208 (1995); and A. Gandjbakhche et al., "Resolution Limits for Optical Transillumination of Abnormalities Deeply Embedded in Tissues," Med. Phys., vol. 21, pp. 185–191 (1994). To achieve optimal resolution, it may be necessary to employ on the order of 100 probes (emitters and detectors). However, for some applications such high resolution may not be needed, for example in diagnosing and localizing strokes. Most strokes are caused by blood vessel occlusions that compromise the blood supply to rather large portion of the brain. Thus the affected area can be adequately located and quantified even with a resolution of a few centimeters. For such applications the number of emitters and detectors needed can be much smaller, thereby reducing cost and increasing imaging speed. A good compromise for some applications between cost and speed on the one hand, and resolution on the other hand, is to image the oxygenation state of tissue in a living human brain at a spatial resolution of about 1 cm.

There is a high degree of variability in the attenuation of light between different emitter-detector pairs. For typical mammalian tissues, signal attenuation in the NIR spectrum is close to 1 optical density unit/cm. The pulse amplitudes received at each collector site can therefore vary by orders of magnitude depending on their respective distances to the emitters, and the "optical thickness" of the intervening tissue. Consequently, the amplitude of some collected signals can be considerably attenuated, or even buried in noise. The signal-to-noise ratio can be improved by boosting the gain of the detector at times (and only at times) corresponding to the anticipated arrival of weak pulses. For example, in the embodiment illustrated in FIG. 3, the gain for detector 102 should be boosted during the arrival of pulses from emitter 2. Similarly, the gain of detectors 104 and 106 should be boosted during the arrival of pulses from 6 and 4, respectively . This temporally selective gain is preferably accomplished with a separate detector and gain booster 38 for each detector.

A prototype embodiment of the invention has been built. The prototype can be used to generate cross-sectional data for tissue oxygenation and blood volume in animal models along nine optical axes at two wavelengths as shown in FIG. 3. A pair of dye lasers produced output pulses having wavelengths of approximately 820 nm and 750 mn. Comparing the absorbance of a biological sample at these two wavelengths yields information on tissue oxygenation, blood volume, and blood flow, The sample holder in the prototype is a cylinder that accommodates samples up to 7.6 cm in diameter, to be inserted into the ring defined by emitters 2, 4, and 6, and detectors 102, 104, and 106.

Each nitrogen-pumped dye laser output pulse had an energy of about 5 $\mu J$, and a duration of about 500 picoseconds at 750 or 820 nm. The outputs of signals arriving at the photodetectors (R928 PMT, Hamamatsu, N.J.) were captured by a fast digitizing oscilloscope (HP 54616B, 500 MHz 2 gigasamples/sec, Hewlett Packard, Englewood, Colo.). The emitter optical fibers (SG365-ler, 3M, West Haven, Conn.) were trimmed so that the light pulses from successive emitters were about 25 nanoseconds apart.

The photomultiplier gain was boosted for weak signals by injecting a high-voltage square pulse lasting 50 ns between the photocathode and the second dynode in each of the three photomultipliers, The sudden increase in gain was timed to correspond to the arrival of the weakest signal at each detector. Boosting the photomultiplier gain only at a time when a weak signal is expected is a method to capture data that might otherwise be lost. The weakest signals are those that have traversed the entire thickness of the sample, and that therefore carry significant information about the central region of the sample (for example, along planes 2-102, 4-106, and 6-104 in FIG. 3). It is easier technically to boost signals if each detector feeds to a separate photomultiplier 38 as illustrated in FIG. 3, so that each detector observes only one signal corresponding to traversing the entire sample during each iteration. (An alternative method of boosting gain is discussed below.)

The delivery of near-infrared, short pulses through multiple optical fibers (fibers 2, 4, and 6) was tested. When pulses transmitted through the fibers (SG365-ler, 3M, West Haven, Connecticut) were directly observed with PMTs, the rise time of the signals remained unchanged as the fiber lengths increased up to 167 feet (corresponding to delays up to 250 ns). Thus the use of long fibers did not interfere with the ability of PMTs to acquire time-resolved information. Attenuation of light through these fibers (~5 db/km) was insignificant for the lengths of fibers considered here. Much longer fibers may therefore be incorporated, allowing a greater number of delivery fibers and correspondingly higher imaging resolution.

We also confirmed the ability of the PMTs to boost gain within a 50 nanosecond window. DC voltages of −950 and −990 volts were applied to the photocathode and second dynode of a PMT (R928, Hamamatsu, N.J.), respectively. The higher voltage at the dynode produced a low gain in the photomultiplier tube. The voltage at the second dynode was then dropped suddenly by adding 200 volts for a duration of 50 nanoseconds using a high-voltage pulser (HV 1000, Directed Energy Inc., Fort Collins, Colo.) and bias circuitry (ST2 and BT1, Directed Energy Inc., Fort Collins, Colo.). This 50 nanosecond voltage pulse produced an increase in gain by a factor of over 400. Even higher changes in gain would result from larger applied voltages. See, e.g., M. Rossetto et al., "A Simple Nanosecond Gate for Side Window Photomultipliers and Echoes in Such Photomultipliers," Rev. Sci. Instr., Vol. 43, pp. 1244–1246, (1972). We observed that the sudden change in gain was accompanied by the production of noise, as had been reported by M. Rosetto et al. The noise, which was of the same order of magnitude as the signal, was reproducible and could therefore be subtracted from the data. A problem encountered in this embodiment was a delay of about 20–30 ns between the voltage change at the dynode and the actual change in gain. This problem may be overcome by earlier triggering of the voltage pulse or increased length of optical fibers.

The prototype embodiment could generate an image within 150 nanoseconds, corresponding to the time to capture 18 probing pulses spaced 25 nanoseconds apart. This period corresponds to a theoretical maximum imaging bandwidth of 6 megahertz. In fact, the prototype embodiment can only achieve this bandwidth when signals are acquired in repetitive mode. The rate-limiting factor in the prototype embodiment was not the data-collecting apparatus itself, but the oscilloscopes used to date. These oscilloscopes could not transfer data to the computer at a rate exceeding 5 waveforms per second. Thus the oscilloscopes limited the effective bandwidth of the prototype embodiment to 5 Hertz in real-time mode. This bandwidth limitation may be readily overcome by using other types of digitizers with an internal storage buffer that can save thousands of waveforms at rates in the kHz range (e.g., Model 9384L oscilloscope, LeCroy, Chestnut Ridge, N.Y.). See also United States patent application Ser. No. 09/016,916, filed Feb. 2, 1998.

Figure 4:
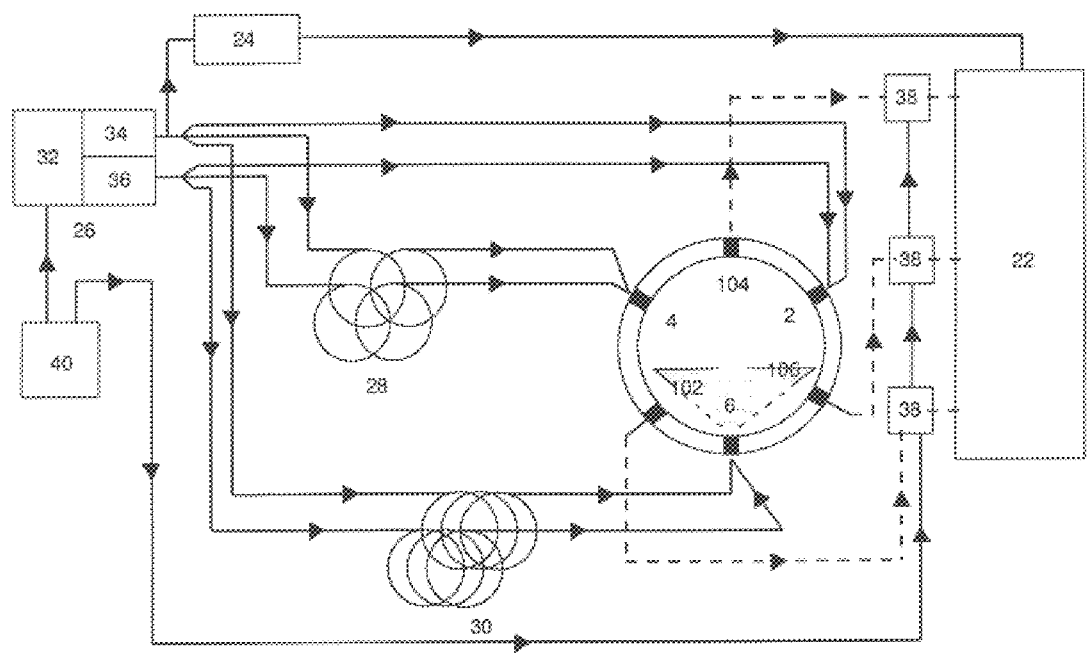
FIG. 4 illustrates another embodiment of a time-resolved tomograph in accordance with this invention, a dual-wavelength, high-bandwidth optical tomograph, in which two laser pulses at each of two frequencies are used per tomographic image.
Figure 5A:
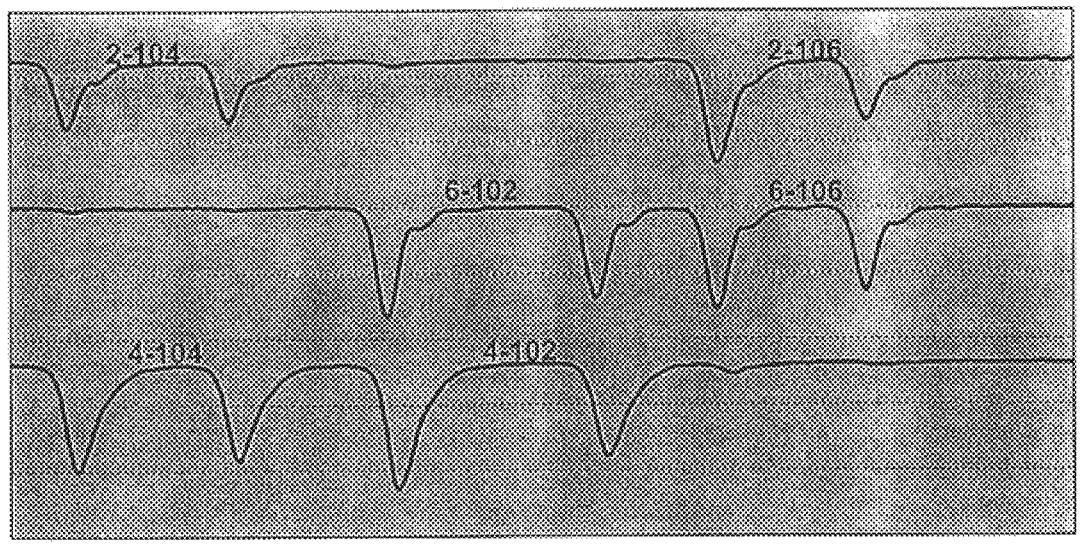
FIGS. 5(*a*) and 5(*b*) depict sample data collected from a sample using a prototype embodiment of the invention, in low-gain and high-gain modes respectively.
Figure 5B:
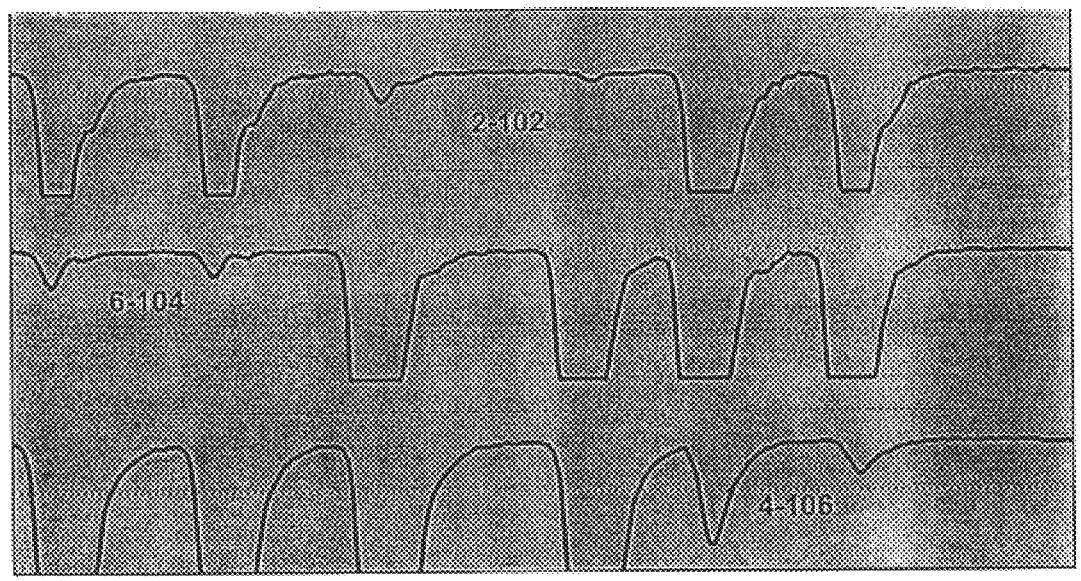

We have recently built another prototype embodiment of the invention. This prototype avoided the noise spike that accompanied the sudden boost in photomultiplier gain of the first prototype described above. Unlike the embodiment of FIG. 3, which produced an image with every laser pulse, this alternative embodiment used two pulses to generate a full set of imaging data. The new embodiment is illustrated in FIG. 4. A programmable, dual-output pulse-generator 40 controlled the timing of gain controls 38 and of laser 32. Laser 32 was triggered with a time delay sufficiently long to allow the noise from the gain-adjusted photomultiplier tubes to decay completely. The gain was maintained at a constant level throughout the detection of signals. With the first pulse of each pair, the gain of the photomultiplier tubes was set to a low level, suitable for monitoring the intense proximal signals. Example waveforms collected with this low-gain setting are shown in FIG. 5(a). Shortly before laser 32 emitted the second pulse of a pair, the gain of the photomultipliers was set to a high level, appropriate to monitoring the low-intensity distal signals. Example waveforms collected with this high-gain setting are shown in FIG. 5(b).

After the temporal profile of the detected signals has been recorded, the data may be processed with any of a number of tomography algorithms such as are known in the art, to yield qualitative or quantitative images of the concentrations of oxyhemoglobin and deoxyhemoglobin, as well as images of tissue turbidity. For examples of such tomography algorithms, see, e.g., R. Cubeddu et al., "Imaging of Optical Inhomogeneities in Highly Diffusive Media: Discrimination between Scattering and Absorption Contributions," Appl. Phys. Lett., vol. 69, pp 4162–4164 (1996); J. Hebden et al., "Imaging through Scattering Media by the Use of an Analytical Model of Perturbation Amplitudes in the Time Domain," Appl. Opt., vol. 35, pp. 6788–6796 (1996), D. Grosnick et al., "Time-Resolved Imaging of Solid Phantoms for Optical Mammography," Appl. Opt., vol. 36, pp. 221–231 (1997), R. Model et al., "Reconstruction Algorithm for Near-Infrared Imaging in Turbid Media by Means of Time-Domain Data," J. Opt. Soc. Am. A, vol. 14, pp. 313–324 (1997); X. Li et al., "Diffraction Tomography for Biochemical, Imaging with Diffuse-Photon Density Waves," Opt. Lett., vol. 22, pp. 573–575 (plus errata) (1997).

Figure 6A:
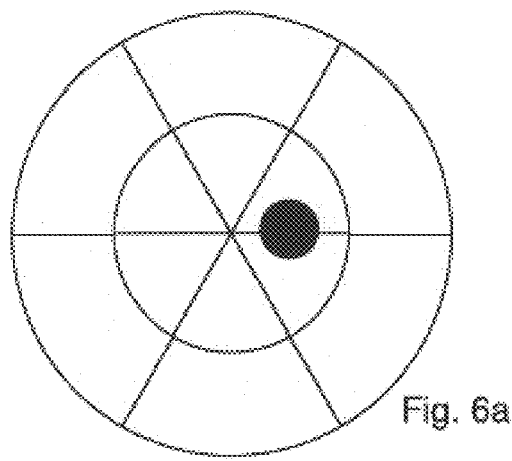
FIG. 6(*a*) depicts the non-biological sample used to test a prototype embodiment of the invention.

A prototype of the system illustrated in FIG. 4 has been evaluated in preliminary laboratory tests on a "dummy" nonbiological cylindrical specimen. The specimen, 7.6 cm in diameter, was constructed from a polyester-based resin containing a titanium dioxide emulsion in a proportion that mimicked the scattering properties of brain tissue (see Kurth et al., Phys. Med. Biol., vol. 40, pp. 2079–2092 (1995)). The sample contained a cylindrical hole, 1.3 cm in diameter, whose center was located 1 cm from the center of the cylinder, as shown in FIG. 6(a). The hole was filled with black ink (Parker Solv X) that is nearly transparent at 820 mn, and that absorbs moderately (1.3 O.D./cm) at 750 cm.

The examples shown in FIG. 5(a) are in fact samples of the transmitted waveforms of this dummy specimen, collected under low gain conditions. Of those signals, the 3 pairs corresponding to the weak distal signals 2-102, 4-106, and 6-104 could not be resolved because of their relatively low intensity. Immediately after the low gain waveforms were saved, pulse generator 40 commanded processing electronics 22 to increase the detector gain. Once the newly-increased gain reached a steady-state, laser 32 was fired again, and a second set of signals recorded. These signals, shown in FIG. 5(b), revealed measurable readings for the distal signals (and photomultiplier saturation for the proximal signals). A full set of imaging data was thus obtained by measuring the proximal signals during the first pulse, and distal signals during the second pulse. Other measurements (not shown) confirmed that the photomultipliers, even when "overloaded" by the strong proximal signals in high-gain mode, recovered in time to respond linearly to the weak distal signals.

Figure 6B:
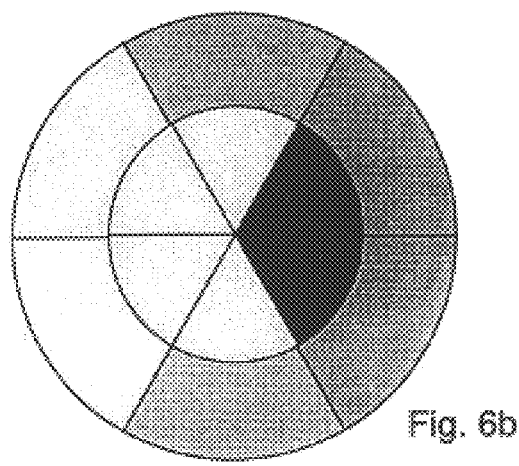
Figure 6C:
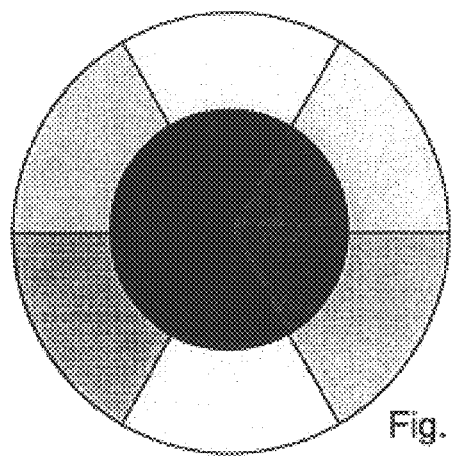

Imaging information can be extracted from the signals shown in FIGS. 5(a) and 5(b) by a variety of procedures known in the art, for example the procedure known as back-projection. In the backprojection approximation, light is assumed to attenuate in accordance to Beer's Law. The sample was divided into 9 sectors, as shown in FIG. 6(a), each with an unknown attenuation coefficient. As each light pulse traversed the sample from an emitter to a detector, its attenuation was equal to the sum of the extinction coefficients of the cells traversed. The attenuation of quasi-ballistic photons was measured by integrating the intensity of the pulses in FIGS. 5(a) and 5(b) during the first 2 nanoseconds of each pulse. The calculated backprojection from these quasi-ballistic transmissions is shown in FIG. 6(b). The number in each sector indicates the calculated attenuation coefficient (O.D. units) for that sector. Note that the sector with the highest attenuation was the sector that contained the occlusion. The importance of collecting data only during a brief temporal window corresponding to quasi-ballistic photons is illustrated by FIG. 6(c), which depicts the same type of calculated backprojection as FIG. 6(b) for the same system depicted in FIG. 6(a), except that the measured photons were those that emerged in a time window between 5 and 7 ns following the emergence of the quasi-ballistic photons.

Alternative embodiments of the invention will use one or more of the following variations of the embodiments described above: making contemporaneous (or near-contemporaneous) measurements with three or more wavelengths of light, to better estimate the pathlength of light through a tissue, or to observe the presence of other pigments such as cytochromes; using a greater number of emitters and detectors to increase resolution; using different geometries than described above; using miniaturized lasers directly at the emitting sites, activated at the appropriate times, without delivery fibers; using miniaturized detectors directly at the detection sites; and replacing the optical trigger with an external pulse generator that triggers both the laser system and the detection system.

This prototype embodiment is expected to image oxygenation states in living tissues at a depth up to 7.5 cm, even when the tissue is surrounded by a bone shell. Initial experiments with biological specimens will use isolated living animal hearts to correlate the effects of ischemic events on the oxygenation and function of heart tissue. Experiments w)ill then extend to living small and large animal models, and ultimately to humans, with all experiments conducted in accordance with pertinent statutes and regulations.

The novel high-bandwidth optical tomograph system of this invention has numerous clinical applications. It may be used for example, to monitor brain oxygenation and blood flow during brain surgery or other surgery, during angioplasty, during stroke or stroke treatment, and to evaluate neurological disorders. It may be used to non-invasively monitor ischemic events in a living heart by localizing variations in hemoglobin oxygen saturation during or after a myocardial infarction, during subsequent intervention, or during a cardiac stress test. The device's ability to collect a complete set of tomographic data and generate near-real-time images at a rate of multiple images per second provides neurologists and psychologists with an novel tool for observing cognitive and other neural processes. The device may be used to locate abnormal inhomogeneities in the brain such as hemorrhage or tumors. The tomograph uses harmless, non-ionizing radiation, is highly amenable to miniaturization, and can even be incorporated into bedside or portable units.

The light detection system should be optimized to detect very small amplitude light signals. NIR photons passing through the head of a child attenuate by about 10 orders of magnitude. To obtain a statistically meaningful measurement of the temporal distribution of photons, a minimum of about one thousand photons should be detected. With a typical detector efficiency of about 10%, a minimum of approximately 10,000 photons would need to be received at each collection site. These figures correspond to the delivery of approximately $10^{14}$ photons per pulse from each emitter site, an energy of about 10 µJ per pulse, The skin can tolerate about 1000 times more energy, spread over 1 cm$^2$, at a rate of 10 pulses per second, without damage or discomfort. Once the radiation enters the body, it diffuses and becomes even less harmful. High-bandwidth NIR optical tomography is readily suited for pediatric uses.

Attenuation of NIR photons through the adult brain ranges from 12 to 16 orders of magnitude. This high level of attenuation implies that the light collection system will likely require signal averaging or time-correlated single photon counting, with integration times between 0.1 and 1000 seconds. See, e.g., F. Jöbsis, "Myocardial Oxygen Sufficiency and Circulatory Parameters," *Science*, vol . 198, pp. 1264–1267 (1977). This lengthy integration time does not necessarily decrease the bandwidth of the imaging system, since many diagnostic tests can be performed repetitively, particularly cognitive and motor tests.

Much of the hardware used in the prototype, such as oscilloscopes, photon counters, and photomultiplier tubes, is now becoming available on PC computer cards. Also, the near-infrared laser system used in the prototype may be replaced with emerging laser technologies, such as a picosecond laser diode with a Ti:sapphire amplifier system to provide shorter pulses with high optical power. Use of such emerging technologies in this invention will allow greater miniaturization and portability, while reducing costs.

The complete disclosures of all references cited in this specification are hereby incorporated by reference. In the event of an otherwise irreconcilable conflict, however, the present specification shall control.

We claim:

1. Apparatus for acquiring tomographic data from a sample, comprising a plurality of at least three emitters, a plurality of at least three detectors, and a timer, wherein:
    (a) each of said emitters is adapted to transmit pulses of collimated, near-infrared laser light to the sample;
    (b) each of said detectors is adapted to detect near-infrared light emerging from the sample in the vicinity of said detector, and to output raw tomographic data corresponding to the time and intensity of infrared light detected by said detector; wherein the gain of each of said detectors is variable, and wherein each of said detectors comprises a booster to temporarily boost the gain of each of said detectors at times corresponding to the arrival of weak near-infrared light pulses emerging, from the sample;
    (c) the positions of said emitters and of said detectors are stationary relative to one another, or said emitters and detectors are adapted to be fixed in positions that are stationary relative to one another;
    (d) said timer is adapted to control the relative timing of the pulses transmitted by said emitters, such that no detector simultaneously detects near-infrared light originating from more than one of said emitters; and such that the relative timing of subsequent pulses from different emitters is between about 5 nanoseconds and about 100 milliseconds; whereby infrared light detected by any one of said detectors at any particular time may be uniquely identified as having, originated from a particular one of said emitters.

2. Apparatus as recited in claim 1, wherein the gain of each of said detectors is variable.

3. Apparatus as recited in claim 2, wherein each of said detectors comprises a photomultiplier.

4. Apparatus as recited in claim 1, additionally comprising a near-infrared laser, and optical fibers of varying lengths optically connecting the output of said laser to each of said emitters; wherein said timer comprises said optical fibers; and wherein the relative timing of laser pulses transmitted by each of said emitters is determined by the relative lengths of said optical fibers.

5. Apparatus as recited in claim 1, wherein said emitters are adapted to transmit pulses of collimated, near-infrared laser light at a plurality of wavelengths.

6. Apparatus as recited in claim 1, wherein said apparatus is adapted to repeat cycles of pulses from each of said emitters, wherein the duration of one cycle is between about 1 microsecond and about 1 second.

7. A method for acquiring tomographic data from a sample, comprising the steps of:

(a) transmitting pulses of collimated, near-infrared laser light to the sample from each of a plurality of at least three emitters; and (b) detecting near-infrared light emerging from the sample in the vicinity of each of a plurality of at least three detectors, and outputting raw tomographic data corresponding to the time and intensity of infrared light detected by each of the detectors; wherein the positions of the emitters and of the detectors are stationary relative to one another; and (c) varying the gain of each of the detectors by temporarily boosting the gain at times corresponding to the arrival of weak near-infrared light pulses emerging from the sample; and (d) controlling the relative timing of the pulses transmitted by the emitters, such that no detector simultaneously detects near-infrared light originating from more than one of the emitters; and such that the relative timing of subsequent pulses from different emitters is between about 5 nanoseconds and about 100 milliseconds; whereby infrared light detected by any one of the detectors at any particular time may be uniquely identified as having originated from a particular one of the emitters.

8. A method as recited in claim 7, additionally comprising the step of varying the gain of each of the detectors.

9. A method as recited in claim 8, wherein each of the detectors comprises a photomultiplier.

10. A method as recited in claim 7, wherein the relative timing of laser pulses transmitted by each of said emitters is determined by the relative lengths of optical fibers of varying lengths optically connecting the output of a near-infrared laser to each of the emitters.

11. A method as recited in claim 7, wherein the pulses of laser light are transmitted at a plurality of wavelengths.

12. A method as recited in claim 7, additionally comprising the step of repeating cycles of step (a) through step (c), wherein the duration of each cycle is between about 1 microsecond and about 1 second.

13. A method as recited in claim 7, wherein said method is used to image a living tissue's blood volume, blood flow, oxygen saturation, cellular depolarization, cellular repolarization, or redox state.

14. A method as recited in claim 13, wherein said method is used to image the oxygenation state of tissue in a living human brain at a spatial resolution of about 1 cm.

15. A method as recited in claim 7, additionally comprising the step of processing the acquired tomographic data to produce an image of the sample.

* * * * *